United States Patent [19]

Chester et al.

[11] Patent Number: 4,574,043

[45] Date of Patent: Mar. 4, 1986

[54] CATALYTIC PROCESS FOR MANUFACTURE OF LOW POUR LUBRICATING OILS

[75] Inventors: Arthur W. Chester, Cherry Hill; William E. Garwood, Haddonfield, both of N.J.; James C. Vartuli, West Chester, Pa.

[73] Assignee: Mobil Oil Corporation, New York, N.Y.

[21] Appl. No.: 673,060

[22] Filed: Nov. 19, 1984

[51] Int. Cl.[4] .................. C10G 45/62; C10G 45/64; C10G 65/12

[52] U.S. Cl. ........................ 208/59; 208/97; 208/111

[58] Field of Search .............. 208/111, 58, 59, 7; 502/77

[56] References Cited

U.S. PATENT DOCUMENTS

| Re. 28,398 | 4/1975 | Chen et al. | 208/111 |
|---|---|---|---|
| 3,530,061 | 9/1970 | Orkin et al. | 208/60 |
| 3,852,207 | 12/1974 | Stangeland et al. | 208/58 |
| 4,031,016 | 6/1977 | Berger et al. | 252/50 |
| 4,137,148 | 1/1979 | Gillespie et al. | 208/87 |
| 4,181,598 | 1/1980 | Gillespie et al. | 208/58 |
| 4,283,271 | 8/1981 | Garwood et al. | 208/59 |
| 4,414,097 | 11/1983 | Chester et al. | 208/59 |
| 4,437,975 | 3/1984 | Gillespie et al. | 208/87 |
| 4,437,976 | 3/1984 | Oleck et al. | 208/97 |
| 4,481,177 | 11/1984 | Valyocsik | 502/77 |

FOREIGN PATENT DOCUMENTS

0101177 2/1984 European Pat. Off. ............ 208/111

Primary Examiner—John Doll
Assistant Examiner—O. Chaudhuri
Attorney, Agent, or Firm—Alexander J. McKillop; Michael G. Gilman; Marina V. Schneller

[57] ABSTRACT

The invention relates to a process for catalytically hydrodewaxing hydrocarbon feedstocks over zeolite ZSM-22 to produce high yields of low pour, high viscosity index hydrocracked lubricating oil stock.

13 Claims, 5 Drawing Figures

CATALYTIC PROCESS FOR MANUFACTURE OF LOW POUR LUBRICATING OILS

BACKGROUND OF THE INVENTION

1. Field of the Invention

This invention relates to a process for manufacture of lubricating oils. In particular, it relates to a specific hydrodewaxing process with high energy and other efficiencies and to production of a hydrocracked lube oil of good stability and low pour point and high viscosity index.

2. Prior Art

Because lubricating oils for the most part are based on petroleum fractions boiling above about 230° C. (450° F.), the molecular weight of the hydrocarbon constituents is high and these constituents display almost all conceivable structures and structure types. The complexity of the molecular constitution of lubricating oils and its consequences are referred to in "Petroleum Refinery Engineering", by W. L. Nelson, McGraw Hill Book Company, Inc., New York, N.Y., 1958 (Fourth Edition), relevant portions of this text being incorporated herein by reference, for background.

Although the broad principles involved in refining are qualitatively understood, the art is encumbered by quantitative uncertainties which require considerable resort to empiricism in practical refining. Underlying these quantitative uncertainties is the complexity of the molecular constitution of lubricating oils. Accordingly, the art of refining suitable petroleum crude oils to obtain a variety of lubricating oils which function effectively in diverse environments has become highly developed and complex.

In general, the basic notion in lubricant refining is that a suitable crude oil, as shown by experience or by assay, contains a quantity of lubricant stock having a predetermined set of properties such as, for example, appropriate viscosity, oxidation stability, and maintenance of fluidity at low temperatures. The process of refining to isolate that lubricant stock consists of a set of subtractive unit operations which removes the unwanted components. The most important of these unit operations include distillation, solvent refining, and dewaxing, which basically are physical separation processes in the sense that if all the separated functions were recombined, one would reconstitute the crude oil.

Unfortunately, crude oils suitable for the manufacture of lubes are becoming less available due to exhaustion of reserves, and the reliability of a steady, adequate supply from a known source is a matter of concern.

The desirability of upgrading a crude fraction normally considered unsuitable for lubricant manufacture to one from which good yields of lubes can be obtained has long been recognized. The so-called "hydrocracking process", sometimes referred to in the art as "severe hydrotreating", has been proposed to accomplish such upgrading. In this process, a suitable fraction of a poor grade crude, such as a California crude, is catalytically reacted with hydrogen under pressure. The process is complex in that some of the oil is reduced in molecular weight and made unsuitable for lubes, but concurrently a substantial fraction of the polynuclear aromatics is hydrogenated to form naphthenes and paraffins. Process conditions and choice of catalyst are selected to provide an optimal conversion of the polynuclear aromatic content of the stock, since this component degrades the viscosity index and stability of the stock.

Also, in the hydrocracking process, paraffins can be isomerized, imparting good viscosity index characteristics to the final lube product. For purposes of this invention, the term "hydrocracking" will be employed for the foregoing process step and to distinguish this step from the "hydrotreating" step to be described below, the purpose of the latter being to stabilize the lube base stock produced by hydrocracking. For purposes of this invention, the hydrocracking and hydrotreating steps may be distinguished also by the amount of hydrogen consumed, the hydrocracking step typically consuming about 1000-2000 SCF/bbl (standard cubic feet per barrel of feed) while the hydrotreating step consumes only about 100-200 SCF/bbl.

The hydrocracking process for increasing the availability of lube oils has an attractive feature that is not immediately apparent. Generally, the composition and properties of hydrocracked stocks are not particularly affected by the source and nature of the crude, i.e. they tend to be much more alike than fractions prepared from different crudes by conventional means. Thus, the process promises to free the refiner from dependence on a particular crude, with all of the advantages that this freedom implies.

Hydrocracked lube stocks, however, tend to be unstable in the presence of air when exposed to sunlight. On such exposure, a sludge is formed, sometimes very rapidly and in fairly substantial amount. This tendency in a lubricating oil is unacceptable. Additionally, some hydrocracked lube oils tend to darken or to form a haze.

Several methods have been proposed to correct the above-described instability. U.S. Pat. No. 4,031,016 proposes to add certain antioxidants to the hydrocracked oil. A second proposed approach is to hydrotreat the hydrocrackate. Variants of this approach are described in U.S. Pat. No. 3,666,657 which teaches a sulfided mixture of an iron group metal and a Group VI metal for the hydrotreating stage; U.S. Pat. No. 3,530,061 which utilizes a hydrotreating catalyst having one or more elements from Group IIB, VIB and VIII at hydrogen pressure up to about 100 psig; and U.S. Pat. No. 4,162,962 which teaches to hydrotreat the hydrocrackate at a temperature in the 200° C. to 300° C. range with a catalyst of prescribed pore size. U.S. Pat. No. 3,530,061 teaches a non-cracking support for the hydrotreating stage. U.S. Pat. No. 3,852,207 teaches to hydrotreat with a noble metal hydrogenation component supported on an oxide. The patents cited above are believed representative of the state of the art, and each is incorporated herein by reference.

Hydrocracked lubricating oils generally have an unacceptably high pour point and require dewaxing. Solvent dewaxing is a well-known and effective process but expensive. More recently catalytic methods for dewaxing have been proposed. U.S. Pat. No. Re. 28,398 describes a catalytic dewaxing process wherein a particular crystalline zeolite is used. To obtain lubricants and specialty oils with outstanding resistance to oxidation, it is often necessary to hydrotreat the oil after catalytic dewaxing, as illustrated by U.S. Pat. No. 4,137,148. U.S. Pat. Nos. 4,283,271, 4,283,272 and 4,414,097 describe processes for producing dewaxed lubricating oil base including hydrocracking a hydrocarbon feedstock catalytically dewaxing the hydrocrackate and hydrotreating the dewaxed hydrocrackate. These latter patents, recognized as advances in the art, describe use of catalyst compositions comprising zeolite ZSM-5, ZSM-11 and ZSM-23 for the dewaxing phase. U.S. patent application Ser. No. 587,327 filed Mar. 7, 1984, a division of U.S. Ser. No. 373,451 filed Apr. 30, 1982, describes ZSM-22 and its use in gas oil dewaxing and lube stock dewaxing. The foregoing patents and U.S. patent application Ser. No. 587,327 indicate the state of the dewaxing art and are incorporated herein by reference as background.

It is inferentially evident from the foregoing background material that, in general, the manufacture of modern high quality lubricants requires that the crude be treated in a sequence of fairly complex and costly steps. It is further evident that there is a need for processes which can efficiently provide such lubricants from interchangeable and readily available low grade crudes.

It is an object of the present invention to provide an improved process for dewaxing a hydrocrackate and for the manufacture of hydrocracked lubricating oils. It is a further object to provide a method for manufacturing hydrocracked lubricating oils having a low pour point and good resistance to light. It is a further object of this invention to provide an energy-efficient process for manufacturing hydrocracked lubricating oils. These and other objects will become evident to one skilled in the art on reading this entire specification including the appended claims.

SUMMARY OF THE INVENTION

This invention provides an energy-efficient process for hydrodewaxing and for manufacturing a stabilized and dewaxed hydrocracked lubricating oil stock from a hydrocarbon feedstock effluent boiling over about 550° F. The process comprises passing such an effluent through a catalytic hydrodewaxing process in which the supported catalyst composition comprises zeolite ZSM-22 and a group VIII metal, preferably platinum. Various advantages are inherent in the process of the invention. The yield of dewaxed oil is higher than those of prior art methods. The viscosity index (VI) of the dewaxed oil produced in accordance with the invention is higher than that obtained by methods employing other catalyst compositions containing zeolites in dewaxing. Activity and selectivity, as measured by viscosity index and lube yield at a given pour point, of the catalyst composition are superior. In addition, the hydrodewaxing conditions include temperatures which are comparable to those of hydrocracking; accordingly, when the effluent processed in accordance with the invention has been previously subjected to hydrocracking and then subjected to hydrodewaxing as described herein, the small temperature differential between hydrocracking and hydrodewaxing, if such temperature differential exists at all, minimizes the need for quenching hydrocrackate effluent from the hydrocracking stage resulting in substantial energy saving.

DETAILED DESCRIPTION OF THE INVENTION

The process of the invention will be described with reference to the flow diagram of FIG. 1 and the embodiment illustrated thereby.

Hydrocracking is undertaken in hydrocracker 3. The feed to the hydrocracker is introduced via line 1 together with hydrogen via line 2 to hydrocracker 3. Hydrocracker 3 includes a catalytic hydrocracking zone maintained at conditions effective to convert in a single pass at least 20% of the feed to materials boiling below the initial boiling point of said feed. Such conditions for the hydrocracking step are summarized in Table I:

TABLE I

|  | Hydrocracking |
|---|---|
| Pressure, broad, psig | 1000–3000 |
| Pressure, preferred | 1500–2500 |
| Temperature, broad, °C. | 260–482 |
| Temperature, preferred, °C. | 343–427 |
| LHSV,* broad | 0.1–5 |
| LHSV, preferred | 0.5–2 |
| $H_2$ gas, SCF/bbl,** broad | 1000–20,000 |
| $H_2$ gas, SCF/bbl, preferred | 2000–10,000 |

A wide variety of hydrocracking catalysts are contemplated as suitable for use in the process of this invention. Such catalysts in general possess an acid function and a hydrogenation function, exemplified by a porous acidic oxide such as a silica alumina or silica zirconia associated with a nickel-tungsten or palladium or platinum, or cobalt-molybdenum or nickel-molybdenum component. In general, a Group VIII metal or a combination of a Group VI and a Group VIII metal, as the oxides or sulfides thereof, deposited on silica alumina or silica zirconia, may serve as hydrocracking catalyst. The hydrocracking itself may be conducted in two or more stages, with pretreatment of the raw feed as part of the first stage.

The effluent from the hydrocracker 3 including excess hydrogen may be contaminated with free hydrogen sulfide and in some cases with ammonia, since the hydrocracking step, in addition to saturating aromatic compounds, also is accompanied by desulfurization and denitrogenation. This effluent may be passed via line 4 to a high pressure gas-liquid separator (G/L Sep) 5 wherein the hydrocrackate is separated from contaminated hydrogen. The contaminated hydrogen may be passed from separator 5 via line 6 to a high pressure sorption section 7 wherein a substantial fraction of the hydrogen sulfide and of the ammonia are removed via line 8.

The hydrogen from sorption unit 7 may be passed via line 9 to a high pressure separator section 10 wherein it is separated from light hydrocarbons which are removed via line 11.

The hydrocrackate separated in separator section 5 is passed via line 12 to catalytic dewaxing section 13 along with makeup hydrogen introduced via line 14. It is important to note for purposes of this invention that the only hydrogen supplied to the catalytic dewaxer section 13 is fresh hydrogen having a hydrogen sulfide partial pressure of less than about 5 psia and less than 100 ppm of ammonia. The amount of hydrogen supplied via line 14 may be up to about the amount consumed in the process. Thus, all of the makeup hydrogen may be supplied via line 14. Alternatively, if it is desired to supply to the catalytic dewaxer 13 less than the makeup requirement of the system, the remainder may be supplied to the hydrocracker via line 15, or at any other point in the system.

Process conditions in the catalytic dewaxer 13 are summarized in Table II

TABLE II

|  | Dewaxing Conditions |
| --- | --- |
| Pressure, broad, psig | 200–3,000 |
| Pressure, preferred | 1,500–2,500 |
| Temperature, broad, °C. | 260–482 |
| Temperature, preferred, °C. | 343–427 |
| LHSV,* broad | 0.2–20 |
| LHSV, preferred | 0.5–5 |
| H₂ gas, SCF**/bbl, broad | 500–20,000 |
| H₂ gas, SCF/bbl, preferred | 500–3,000 |

*LHSV = liquid hourly space velocity, i.e. volumes of feed per volume of catalyst per hour.
**SCF/bbl = standard cubic feet per barrel.

The catalyst composition used in dewaxing section 13 comprises about 47 to about 80 weight percent ZSM-22, in combination with the Group VIII metal(s) and support material. ZSM-22 is a highly siliceous zeolite which can be prepared from a reaction mixture comprising a source of silica, an alkali metal oxide or an alkaline earth metal oxide, e.g., sodium, potassium, cesium, calcium or strontium, water, and alumina. In addition, the reaction mixture will preferably contain a template or directing agent. The template or directing agent may be selected from a variety of organic compounds. Amines and alcohols may act as such template or directing agents. Preferred directing agents are the alkane diamines or their salts and the dialkylammonium compounds. When the organic compound is alkene diamine the reaction mixture will have a composition, in terms of mole ratios of oxides, falling within the following ratios:

| Reactants | Broad | Preferred | Most Preferred |
| --- | --- | --- | --- |
| $SiO_2/Al_2O_3$ = | 20 to ∞ | 30 to 1000 | 60 to 200 |
| $H_2O/SiO_2$ = | 10 to 100 | 20 to 60 | 20 to 60 |
| $OH^-/SiO_2$ = | 0 to 0.3 | 0.1 to 0.2 | 0.1 to 0.2 |
| $M^+/SiO_2$ = | 0 to 2.0 | 0.1 to 1.0 | 0.1 to 1.0 |
| $RN/SiO_2$ = | 0.1 to 2.0 | 0.05 to 1.0 | 0.05 to 1.0 | wherein RN is a $C_2$–$C_{12}$ alkane diamine of the formula $H_2N$-$(CH_2)_n$-$NH_2$ (abbreviated $C_nDN$), n=2 to 12, and preferably is 5 to 8, and M is an alkali metal or an alkaline earth metal, as described in U.S. Ser. No. 373,452, filed Apr. 30, 1982, which is incorporated by reference herein.

Suitable diamines are, e.g., ethanediamine, propanediamine, butanediamine, pentanediamine, hexanediamine, heptanediamine, octane-diamine, nonanediamine, decanediamine, undecanediamine, duodecane-diamine. In the as-synthesized form, the ZSM-22 has a calculated composition, in terms of moles of oxides, after dehydration, per 100 moles of silica, as follows:

$$(0.02 \text{ to } 10)RN:(0 \text{ to } 2)M_{2/n}O:(0 \text{ to } 5)Al_2O_3:100SiO_2$$

wherein RN is a $C_2$–$C_{12}$ alkane diamine and M is an alkali metal or an alkaline earth metal having a valence n, e.g., Na, K, CS, Li, Ca or Sr.

Suitable dialkylammonium compounds which may be used as the organic compound acting as the template or directing agent are those in which each of the alkyl groups is the same or different and each alkyl group has two (2) to eight (8) carbon atoms, e.g., ethyl, propyl, butyl, pentyl, hexyl, heptyl or octyl. Synthesis of ZSM-22, in which dialkylammonium compound is used as the directing agent, is described in Ser. No. 373,451 filed Apr. 30, 1982, which is incorporated by reference herein. In the as synthesized form, using a dialkylammonium source, the ZSM-22 has a calculated composition, in terms of moles of oxides, after dehydration, per 100 moles of silica, as follows:

$$(0.01-2.0)Q_2O:(0-2.0)M_{2/n}O:(0-5)Al_2O_3:100SiO_2$$

wherein $Q_2O$ is the oxide form of said dialkylammonium. It is believed that either polyalkylene polyamines or methanol in appropriate mole ratios, based on the moles of reactants, may also be used as the directing agent to produce ZSM-22.

The reaction mixture is maintained at crystallization temperature until crystals of the ZSM-22 zeolite are formed. Thereafter, the crystals are separated from the liquid by any conventional means, washed and recovered. Crystallization can be carried out under either static or stirred conditions in a reactor vessel, e.g., a polypropylene jar, teflon lined or stainless steel autoclaves, at 80° C. (176° F.) to about 210° C. (410° F.) for about 6 hours to 150 days. Thereafter, the crystals are separated from the liquid and recovered. The composition can be prepared utilizing materials which supply the appropriate oxide. Such materials include aluminates, alumina, silicates, sodium silicate, silica hydrosol, silica gel, silicia acid, sodium, potassium or cesium hydroxide, and an alkane diamine. The reaction mixture can be prepared either batchwise or continuously. Crystal size and crystallization time of the crystalline material varies with the nature of the reaction mixture employed and the crystallization conditions.

As set forth above, the ZSM-22 zeolite can be prepared at a relatively wide range of $SiO_2/Al_2O_3$ ratios of about 20 to about infinity ∞. However, it has been found that larger alkali metal cations, e.g., $K^+$ and $Cs^+$, are preferably used at the $SiO_2/Al_2O_3$ ratios of about 20 to about 90 to obtain ZSM-22 crystals substantially free of impurities or other zeolites. The potassium ($K^+$) cation is preferred at such low $SiO_2/Al_2O_3$ ratios because cesium (Cs) appears to decrease the reaction rate. At the $SiO_2/Al_2O_3$ ratios of 90 or above, e.g., 90 to 200, smaller cations, e.g., sodium ($Na^+$) cations, are preferably used to produce substantially 100% crystalline ZSM-22.

The highly siliceous ZSM-22 zeolite comprises crystalline, three-dimensional continuous framework, silicon-containing structures or crystals which result when all the oxygen atoms in the tetrahedra are mutually shared between tetrahedral atoms of silicon or aluminum, and which can exist with a network of mostly $SiO_2$, i.e., exclusive of any intracrystalline cations. In the as-synthesized form, the ZSM-22 has a calculated composition, in terms of moles of inorganic oxides, after dehydration, per 100 moles of silica, as follows:

$$(0 \text{ to } 2)M_{2/n}O:(0 \text{ to } 5)Al_2O_3:100SiO_2$$

wherein M is an alkali metal or an alkaline earth metal having a valence n, e.g., Na, K, Cs, Li, Ca or Sr and n is 1 or 2.

ZSM-22 can further be identified by its sorptive characteristics and its X-ray diffraction pattern. The original cations of the as-synthesized ZSM-22 may be replaced at least in part by other ions using conventional ion exchange techniques. It may be necessary to precalcine the ZSM-22 zeolite crystals prior to ion exchange. The replacing ions introduced to replace the original alkali, alkaline earth and/or organic cations may be any ions that are desired so long as they can pass through the channels with the zeolite crystals. Desired replacing ions are those of hydrogen, rare earth metals, metals of Groups IB, IIA, IIB, IIIA, IIIB, IVA, IVB, VIB and VIII of the Periodic Table. Among the metals, those particularly preferred are rare earth metals, manganese, zinc and those of Group VIII of the Periodic Table.

ZSM-22 zeolite described herein has a definite X-ray diffraction pattern, set forth below in Table A, which distinguishes it from other crystalline materials.

TABLE A

| Most Significant Lines of ZSM-22 | |
|---|---|
| Interplanar d-spacings (Å) | Relative Intensity |
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and an associated computer were used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplaner spacing in angstroms (A), corresponding to the recorded lines, were determined. In Table I, the relative intensities are given in terms of the following symbols vs=very strong, s=strong, m=medium, w=weak, etc. It should be understood that this X-ray diffraction pattern is characteristic of all the species of ZSM-22 zeolite compositions. Ion exchange of the alkali or alkaline earth metal cations with other ions results in a zeolite which reveals substantially the same X-ray diffraction pattern as that of Table 1 with some minor shifts in interplanar spacing and variations in relative intensity. Other minor variations can occur, depending on the silica to alumina ratio of the particular sample, as well as its degree of thermal treatment.

The ZSM-22 zeolite freely sorbs normal hexane and has a pore dimension greater than about 4 Angstroms. In addition, the structure of the zeolite must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings do not generally appear to offer sufficient constraint to produce the advantageous hydrocarbon conversions, although puckered structures exist such as TMA offretite which is a known effective zeolite. Also, such twelve-membered structures can be conceived that may be operative due to pore blockage or other causes.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted to between 550° F. (288° C.) and 950° F. (510° C.) to give an overall conversion between 10% and 60%. The mixture of hydrocarbons is passed at a 1 liquid hourly space velocity (LHSV), i.e., 1 volume of liquid hydrocarbon per volume of zeolite per hour, over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. The ZSM-22 zeolite has a constraint index of about 2.6 at 800° F. (427° C.). Constraint Index (CI) values for some other typical zeolites are:

| Zeolite | C.I. |
|---|---|
| ZSM-5 | 8.3 |
| ZSM-11 | 8.7 |
| ZSM-12 | 2 |
| ZSM-23 | 9.1 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina (non-zeolite) | 0.6 |
| Erionite | 38 |

It is to be realized that the above constraint index values typically characterize the specified zeolites but that these are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables, such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is an approximation, taking into consideration the manner of its determination, with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina mole ratio. In those instances, a temperature of up to about 1000° F. and a liquid hourly space velocity of less than one, such as 0.1 or less, can be employed in order to achieve a minimum total conversion of about 10%.

The sorption of hydrocarbons by ZSM-22 has been surveyed and the results are summarized in Table B. Sorption capacities for n-hexane (normal hexane), cyclohexane, and water are about 4% by weight, or about one third that of ZSM-5. Cyclohexane and o-xylene sorption is relatively slow, making it difficult to determine equilibrium capacities.

TABLE B

| | | ZSM-22 Sorption Data | | | |
|---|---|---|---|---|---|
| | | Sorptions (Wt %) a | | | |
| Sample | Form | n-hexane | 3-methyl-pentane | Cyclo-hexane | $H_2O$ | o-xylene b |
| 1 | Hydrogen | 3.9 | — | 2.8 | — | — |
| 2 | Hydrogen | 4.2 | 3.9 | 1.1 | — | 2 |
| 3 | Hydrogen | 4.1 | — | 3.3 | 4.7 | — |
| 4 | as-synthesized | 3.4 | — | — | — | — | a Hydrocarbons: vapor pressure = 20 mm Hg, temperature = 25° C.; water-pressure = 12 mm Hg, temperature = 25° C.
b vapor pressure = 3.7 mm Hg, temperature = 120° C.
c slow tailing sorption, nonequilibrium values.

The n-hexane/o-xylene ratios may vary under different conditions, as illustrated by the data of Table C, below:

TABLE C

| Additional Adsorption Properties of ZSM-22 Sample Temperature = 100° C. | | | | |
|---|---|---|---|---|
| Sample | Form | Sorbate | Vapor Pressure (mm Hg) | $P/P_o$ | Wt % sorbed |
| 5 | Hydrogen | o-Hexane | 80 | 0.04 | 4.0 |
| 6 | Hydrogen | o-Xylene | 5 | 0.025 | 1.1 |

The ZSM-22 zeolite, as synthesized, tends to crystallize as agglomerates of elongated crystals having the size of about 0.5 to about 2.0 microns ($\mu$). Ballmilling fractures these crystals into smaller size crystallites (about 0.1$\mu$) without significant loss of crystallinity. The zeolite can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion and described below, the crystals can be extruded before drying or partially dried and then extruded.

The ZSM-22 zeolite can be used either in the organic nitrogen-containing and alkali metal-containing form, the alkali metal form and hydrogen form or another univalent or multivalent cationic form. The as-synthesized zeolite may be conveniently converted into the hydrogen, the univalent or multivalent cationic forms by base exchanging the zeolite to remove the sodium cations by such ions as hydrogen (from acids), ammonium, alkylammonium and arylammonium including $RNH_3$ $R_3NH^{30}$, $R_2NH_2$ and $R_4N^+$ where R is alkyl or aryl, provided that steric hindrance does not prevent the cations from entering the cage and cavity structure of the ZSM-22 type crystalline zeolite. The hydrogen form of the zeolite, useful in such hydrocarbon conversion processes as isomerization of poly-substituted alkyl aromatics and disproportionation of alkyl aromatics, is prepared, for example, by base exchanging the sodium form with, e.g., ammonium chloride or hydroxide whereby the ammonium ion is substituted for the sodium ion. The composition is then calcined at a temperature of, e.g., 1000° F. (about 540° C.) causing evolution of ammonia and retention of the hydrogen proton in the composition. Other replacing cations include cations of the metals of the Periodic Table, particularly metals other than sodium, most preferably metals of Group IIA, e.g., zinc, and Groups IIIA, IVA, IB, IIB, IIIB, IVB, VIB and Group VIII of the Periodic Table, and rare earth metals and manganese.

Ion exchange of the zeolite can be accomplished conventionally, e.g., by admixing the zeolite with a solution of a cation to be introduced into the zeolite. Ion exchange with various metallic and non-metallic cations can be carried out according to the procedures described in U.S. Pat. Nos. 3,140,251, 3,140,252 and 3,140,253, the entire contents of which are incorporated herein by reference.

The Group VIII metal component of the catalyst composition can be exchanged into the composition, impregnated therein or physically and intimately admixed therewith. Ion exchange can be carried out according to procedures described in U.S. Pat. Nos. 3,140,251, 3,140,252 and 3,140,253, the entire contents of which are incorporated by reference herein. Impregnation may be effected by treating the zeolite with a solution containing a Group VIII metal- or a Group VIII metal-containing ion. The amount of Group VIII metal in the catalyst composition can range from about 0.1 to about 3 weight percent, preferably from about 0.2 to about 1 weight percent, based on the total weight of the catalyst composition. The Group VIII metal component can be platinum, palladium, iridium, ruthenium, cobalt, nickel and mixtures thereof. The preferred Group VIII metal is platinum or palladium. Although Platinum is the most preferred Group VIII metal used in the catalyst composition, it is contemplated that a Group VIII metal other than platinum, can be used to replace platinum at least in part in the catalyst composition; the preferred Group VIII metal component replacing platinum is one which effects a result equivalent to platinum in combination with the ZSM-22 zeolite of the catalyst composition of the invention. The Group VIII metal component of the composition may be used alone or in combination with a metal from Group VI of the Periodic Table of Elements. Examples of metals of Group VI are chromium, molybdenum, tungsten and mixtures thereof.

The catalyst composition comprising the zeolite ZSM-22 dewaxing catalyst component and Group VIII metal(s) includes a support material which is matrix or binder component comprising a material resistant to the temperature and other process conditions.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee, Ga. and Florida clays or others in which the main mineral constituent is halloysite, kaolinite, nacrite or anauxite. Such clays can be used in the raw state as originally mined or initially subjected to calcination, acid treatment or chemical modification.

In addition to the foregoing materials, the zeolite ZSM-22 employed herein may be composited with a porous matrix material, such as alumina, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel.

The relative proportions of zeolie ZSM-22 component ang Group VIII metal and support material on an anhydrous basis, may vary widely. The support material content will range from about 20 to about 50 percent by weight and is more usually in the range of about 25 to about 45 percent by weight of the dry composite; preferably the support comprises 30 to 40 percent by weight of the dried composite. The preferred supports of the catalyst composition are alumina, silica and silica-alumina.

The Group VIII component associated with ZSM-22 may be on the zeolite component as above-noted or on the matrix component or both.

Since each of the hydrocracking and hydrodewaxing operations may produce oils unstable to air and/or to light, the invention embraces a hydrotreating operation subsequent to the hydrodewaxing operation. To undertake the hydrotreating operation, the effluent from the catalytic dewaxer 13, including excess hydrogen, can be passed via line 16 to hydrotreater unit 17. Catalytic hydrotreater 17 contains a hydrotreating catalyst in a hydrotreating zone at stabilizing conditions. Examples of hydrotreating catalysts include, without limitation, one or more metals from Group VIII (e.g. cobalt and nickel) and Group VI (e.g. molybdenum and tungsten) of the Periodic Table of Elements supported by an inorganic oxide such as, for example, alumina or silica-alumina. Conditions in the hydrotreater unit 17 are summarized in Table III:

TABLE III

|  | Hydrotreating Conditions |
|---|---|
| Pressure, broad, psig | 1000–3000 |
| Pressure, preferred | 1500–2500 |
| Temperature, broad, °C. | 176–371 |
| Temperature, preferred, °C. | 204–316 |
| LHSV,* broad | 0.1–10 |
| LHSV, preferred | 0.2–3 |
| $H_2$ gas, SCF/bbl, broad | 500–20,000 |
| $H_2$ gas, SCF/bbl, preferred | 500–3000 |

By disposing the catalytic dewaxing step between the hydrocracking and stabilization step in the manner described in this embodiment, a very efficient over-all process results with the production of a stabilized and dewaxed hydrocracked lubricating oil stock.

Figure 1:
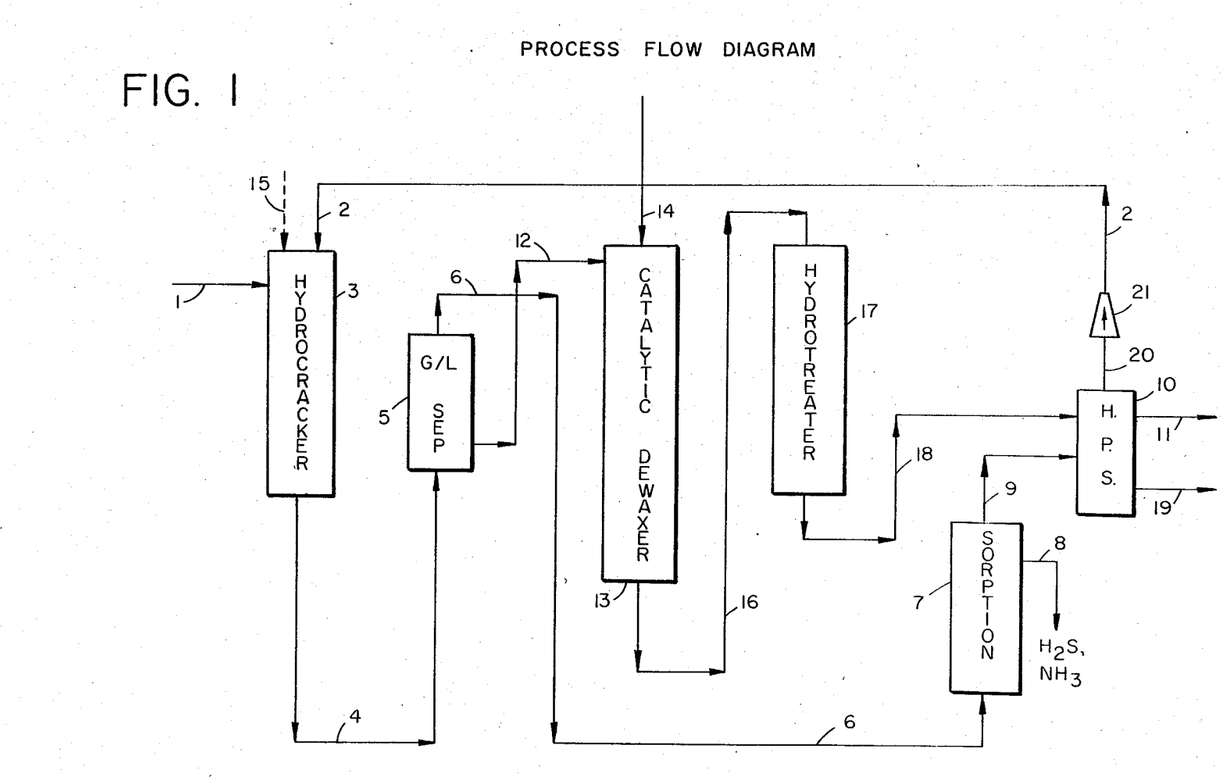
FIG. 1 is a process flow diagram illustrating the process of the invention.

The embodiment shown in FIG. 1 of the process of this invention is illustrative of processing a hydrocarbon oil by the sequence of steps comprising hydrocracking, catalytic dewaxing by the present method and stabilization, in that order, with only fresh hydrogen provided to the catalytic dewaxer.

The effluent from the hydrotreater unit is passed via line 18 to a high pressure separation section 10 wherein it is treated to separate light hydrocarbons, which are removed together with a hydrogen bleed via line 11. Also separated is the hydrocarbon mixture comprising a stabilized and dewaxed hydrocracked lubricating oil stock, which is recovered via line 19. The hydrocarbon mixture containing the lubricating oil stock is passed via line 19 to another unit for recovery of the lubricating oil stock, which other unit is not part of this invention. The makeup and recycle hydrogen separated in section 10 is passed via line 20 to compressor 21 to raise its pressure and then passed via line 2 to the hydrocracker 3.

Preferably, the pressure in line 20, which is downstream from pump 21, and the pressure in line 2, which is upstream of pump 21, do not differ by more than about 750 psig.

It will be recognized by those skilled in the art that various separation steps conducted at high pressure may be advantageously incorporated in the process flow diagram of FIG. 1. For example, a high pressure separation unit may be located in line 12 or line 16, for example, to remove a low molecular weight fraction of hydrocarbon not suitable for inclusion in the final lubricant base stock, thereby reducing the hydrocarbon load to subsequent sections.

EXAMPLES

The charge stock in Examples 1–3 was a hydrocracked stock from Idemitsu having the following properties:

| Gravity, °API | 31.9 |
|---|---|
| Specific | 0.8660 |
| Pour Point, °F. | +90 |
| KV @ 100° C., cs | 5.02 |
| Hydrogen, wt % | 14.21 |
| Sulfur, ppm | 26 |
| Nitrogen, ppm | <5 |
| Boiling Range, D-2887 | |
| 1% | 620 |
| 5 | 681 |
| 10 | 707 |
| 30 | 767 |
| 50 | 811 |
| 70 | 850 |
| 80 | 893 |
| 90 | 913 |
| 95 | 943 |

In each of the examples, the 1/16" extruded catalysts were sized to 14–25 mesh, 5 cc charged to the stainless steel reactor, and reduced with hydrogen at 900° F., atmospheric pressure, for one hour before introduction of the oil. Standard run conditions were 400 psig, 1 LHSV (liquid hourly space velocity), 2500 SCF (standard cubic feed per barrel of feed) $H_2$/bbl, and temperature varied to obtain the desired pour point.

Example 1

The catalyst was prepared by adding $Pt(NH_3)_4Cl_2$ to 65/35 ZSM-5/$Al_2O_3$ and extruding the mixture. The ZSM-5 component was B crystal, 70/1 $SiO_2/Al_2O_3$ and the final catalyst after calcination in air at 1000° F. for 3 hours contained 0.50 wt % Pt.

The catalytic results with this catalyst are summarized below.

| Run No. | −1 | −2 | −3 | −4 |
|---|---|---|---|---|
| Av. Cat. Temp., °F. | 526 | 525 | 500 | 476 |
| Mat. Bal., hours | 17.5 | 23 | 22.5 | 22.5 |
| TOS, days | 0.7 | 1.7 | 2.6 | 3.5 |
| Lube Product | | | | |
| Yield, wt % | 75.0 | 76.1 | 75.2 | 82.2 |
| Pour Point | −55 | −45 | −40 | +10 |
| KV @ 40° C. | 38.48 | 38.37 | 36.49 | 33.04 |
| KV @ 100° C. | 5.80 | 5.81 | 5.69 | 5.50 |
| VI | 87.7 | 88.9 | 92.4 | 101.7 |

Example 2

The catalyst was prepared by impregnating HZSM-23 extrudate (65/35 zeolite/$Al_2O_3$), after calcination in air at 1000° F. for 3 hours, with $H_2PtCl_6$. The zeolite component was a 114/1 $SiO_2/Al_2O_3$ ZSM-23 prepared from HiSil and aluminum sulfate. The final catalyst was dried, calcined in air at 900° for an additional 3 hours, and contained 0.56 wt % pt.

| Run No. | 1 | −2 | −3 | −4 | −5 | −6 | −7 | −8 |
|---|---|---|---|---|---|---|---|---|
| Av. Cat. Temp., °F. | 600 | 600 | 551 | 577 | 625 | 601 | 601 | 625 |
| Mat. Bal., hours | 16.5 | 22.5 | 22.5 | 22.5 | 23.0 | 17.0 | 23.0 | 23.0 |
| TOS, days | 0.7 | 1.7 | 2.6 | 3.5 | 4.4 | 5.1 | 6.1 | 7.0 |
| Lube Product | | | | | | | | |
| Yield, wt % | 88.9 | 85.4 | 94.6 | 93.6 | 79.2 | 86.4 | 88.3 | 81.2 |
| Pour Point | −25 | −25 | +65 | +30 | −40 | +5 | +5 | −30 |
| KV @ 40° C. | 27.92 | 29.00 | 27.92 | 28.10 | 31.13 | 29.08 | 28.55 | 29.47 |
| KV @ 100° C. | 4.99 | 5.08 | 5.11 | 5.08 | 5.24 | 5.12 | 5.08 | 5.09 |
| VI | 103.4 | 101.8 | 111.7 | 108.3 | 97.7 | 103.9 | 105.0 | 99.2 |

Example 3

The ZSM-22 extrudate was prepared as follows.

A solution was prepared by mixing one part (by wt) aluminum sulfate, 4.5 parts potassium hydroxide (86% by wt) and 50 parts water. This solution was added to an autoclave. Another solution was prepared by mixing 27.6 parts colloidal silica (30% by wt) and 36 parts water and then this mixture was added to the solution in the autoclave. Six parts of diethylamine hydrochloride was then added and the combined solution was agitated vigorously for approximately one-half hour. The autoclave was heated to 330° F. with constant stirring and maintained for 72 hours at this temperature. The resultant crystalline material was then filtered and washed on a Buchner funnel and then dried overnight at 250° F. The X-ray diffraction analysis indicated that this material was ZSM-22. Chemical analysis gave a silica to alumina molar ratio of 82.

This zeolite was mixed with alpha-$Al_2O_3.3H_2O$ to make a mixture of 65 parts (by wt) zeolite and 35 parts alumina. Enough water was added to the mixture so that the resulting catalyst could be formed into 1/16" extrudates. These extrudates were activated by first calcining in nitrogen at 1000° F., followed by aqueous exchanges with a 1.0N ammonium nitrate solution and finally calcining in air at 1000° F.

The extrudate was impregnated with $H_2PtCl_6$, dried and calcined in air at 900° F. for 3 hours. The final catalyst contained 0.57 wt % Pt.

| Run No. | −1 | −2 | −3 | −4 | −5 | −6 | −7 | −8 |
|---|---|---|---|---|---|---|---|---|
| Av. Cat. Temp., °F. | 599 | 599 | 599 | 601 | 599 | 576 | 625 | 601 |
| Mat. Bal., hours | 22 | 23 | 23 | 23 | 23 | 22 | 22 | 22 |
| TOS, days | 0.9 | 1.9 | 2.8 | 3.8 | 4.7 | 5.6 | 6.5 | 7.4 |
| Lube Product | | | | | | | | |
| Yield, wt %* | 86.8 | 87.1 | 87.7 | 88.4 | 88.8 | 93.2 | 86.4 | 88.7 |
| Pour Point | −35 | −35 | −30 | −30 | −25 | +15 | −30 | −20 |
| KV @ 40° C. | 31.82 | 31.28 | 31.05 | 30.66 | 30.77 | 29.78 | 30.68 | 30.63 |
| KV @ 100° C. | 5.37 | 5.29 | 5.31 | 5.28 | 5.29 | 5.25 | 5.24 | 5.27 |
| VI | 101.5 | 100.1 | 102.8 | 103.4 | 103.3 | 107.4 | 100.9 | 103.0 |

Figure 2:
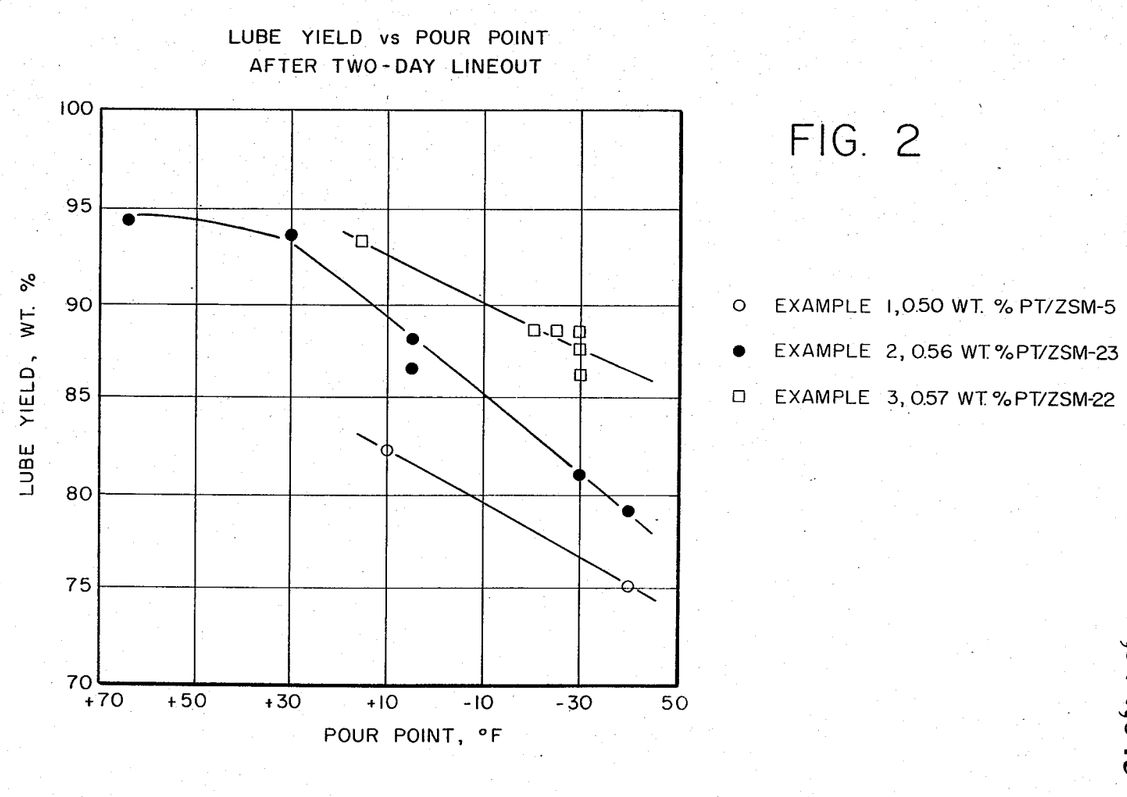
FIG. 2 is a plot of lube product yield in weight percent v. product pour point (°F.).
Figure 3:
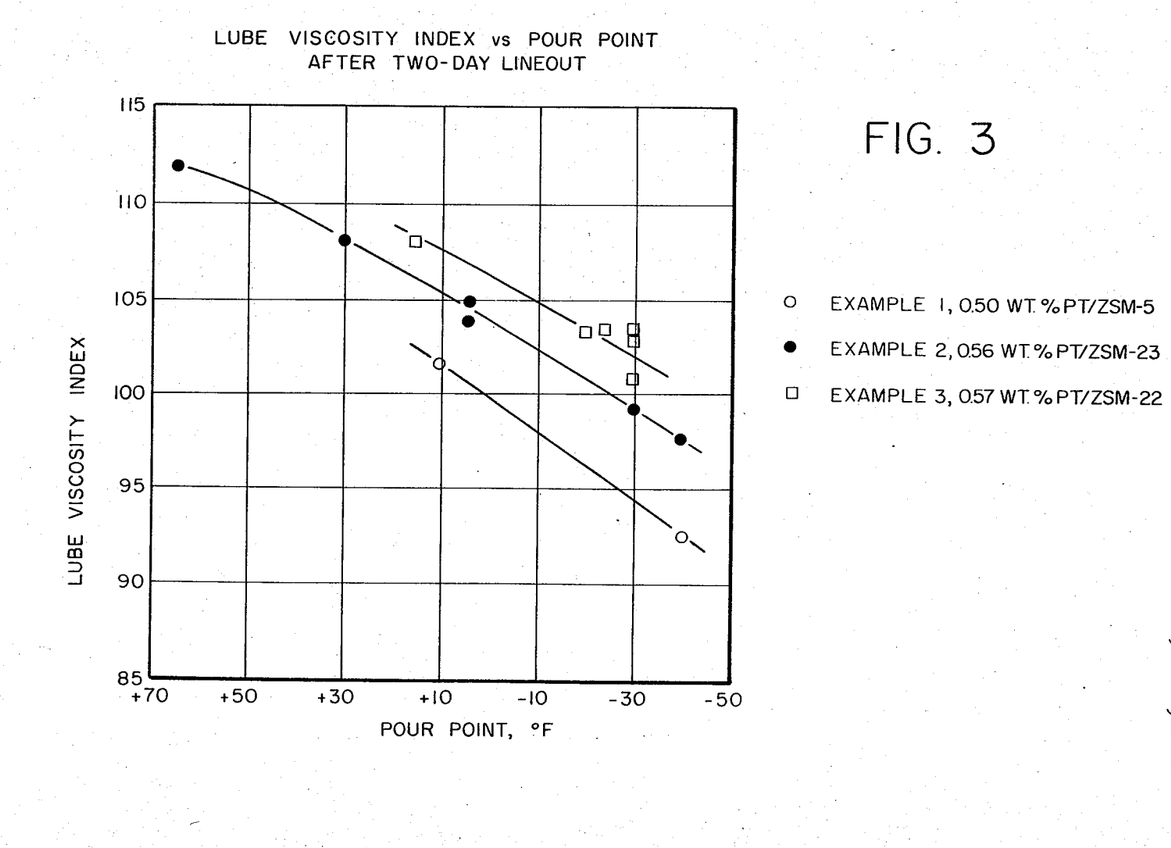
FIG. 3 is a plot of product viscosity index v. product pour point.

Comparison of the three examples shows that the Pt/ZSM-5 catalyst is the most active. However, Pt/ZSM-22 is superior to both Pt/ZSM-5 and Pt/ZSM-23 in both lube yield and VI after a two-day lineout, as shown in FIGS. 2 and 3. The differences, compared at 0° F. pour point from the figures, are as follows:

| | Comparisons at 0. °F. Pour Point | | |
|---|---|---|---|
| Catalyst | 0.50% Pt/ ZSM-5 | 0.56% Pt/ ZSM-23 | 0.57% Pt/ ZSM-22 |
| Lube Yield, wt % | 81 | 87 | 91 |
| Viscosity Index | 100 | 104 | 106 |

Example 4

In this example, solvent refined light neutral stock characterized by the following properties

| Gravity, °API | 32.3 |
|---|---|
| Specific | 0.8639 |
| Pour Point, °F. | +95 |
| K.V. @ 100° C., cs | 4.80 |
| Hydrogen, Wt % | 13.92 |
| Sulfur, Wt % | 0.76 |
| Nitrogen, ppm | 19 |
| Boiling Range, °F., D-2887 | |
| 1% | 653 |
| 5 | 716 |
| 10 | 738 |
| 30 | 778 |
| 50 | 805 |
| 70 | 835 |

-continued

| | |
|---|---|
| 80 | 854 |
| 90 | 888 |
| 95 | 926 |
| 98 | 973 | was subjected to hydrodewaxing using the catalyst described in Example 3, at 400 psig. 1 LHSV, 2500 SCF H₂/bbl. The results of three runs under such conditions are set forth below:

| Run No. | −1 | −2 | −3 |
|---|---|---|---|
| Av. Cat. Temp., °F. | 598 | 675 | 699 |
| Mat. Bal., Hrs. | 18½ | 21.0 | 22 |
| TOS, Days | 8.6 | 9.5 | 10.4 |
| Lube Product | | | |
| Yield, wt % | 94.6 | 88.4 | 86.8 |
| Pour Point, °F. | +60 | +10 | +10 |
| K.V. @ 40° C. | 35.24 | 32.63 | 28.55 |
| K.V. @ 100° C. | 5.98 | 5.51 | 5.09 |
| VI | 114.3 | 104.7 | 105.7 |

Example 5

For purposes of comparison, the solvent refined light neutral stock described in Example 4 was subjected to hydrodewaxing conditions described in Example 4 but the catalyst was replaced by the standard MLDW catalyst, 1.0 wt% Ni/ZSM-5 extrudate, 70 alpha, sulfided in situ. Run results are set forth below:

| | −1 | −2 | −3 | −4 |
|---|---|---|---|---|
| Av. Cat. Temp. °F. | 549 | 549 | 599 | 576 |
| Mat. Bal., Hrs. | 17.0 | 22.0 | 23.0 | 22½ |
| TOS, Days | 0.7 | 1.6 | 2.6 | 3.5 |
| Lube Product | | | | |
| Yield, wt % | 70.1 | 79.4 | 68.9 | 74.9 |
| Pour Point, °F. | −5 | +25 | −35 | −5 |
| K.V. @ 40° F. | 33.06 | 29.38 | 38.07 | 33.11 |
| K.V. @ 100° C. | 5.35 | 5.1 | 5.66 | 5.36 |
| VI | 91.6 | 100.6 | 81.7 | 92.1 |

Figure 4:
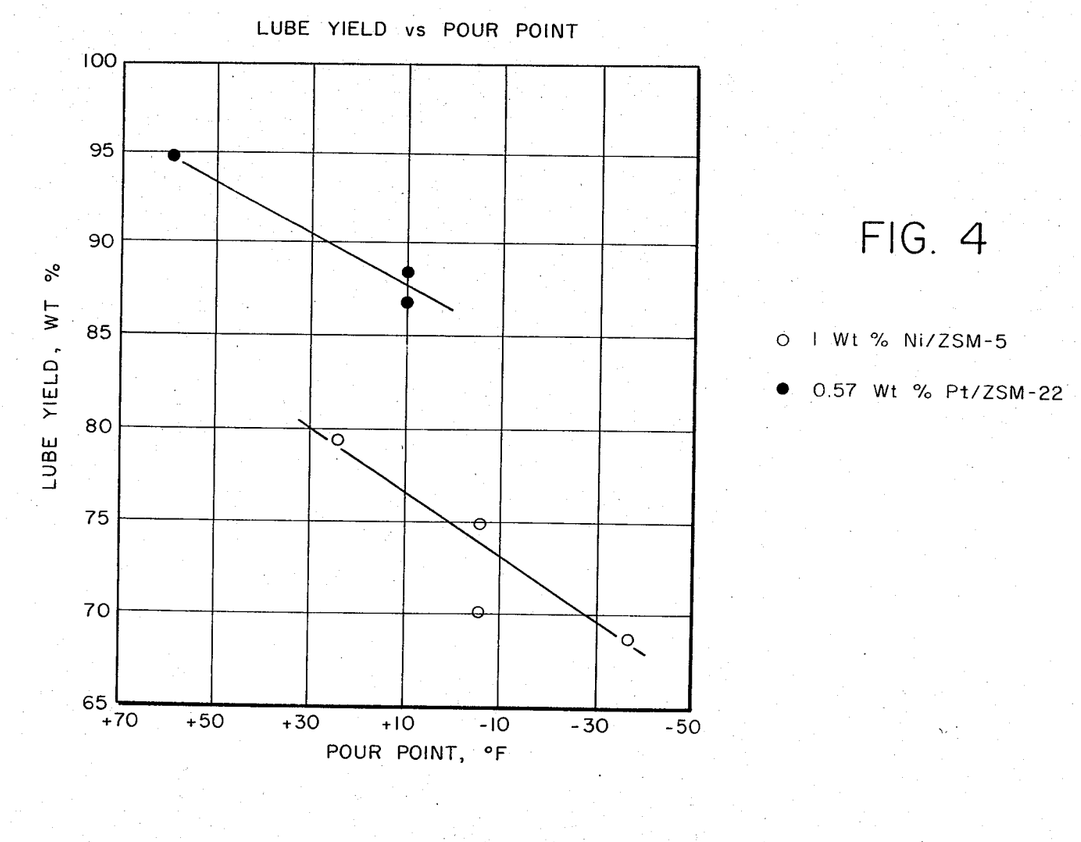
FIG. 4 is a plot of lube product yield v. product pour point.
Figure 5:
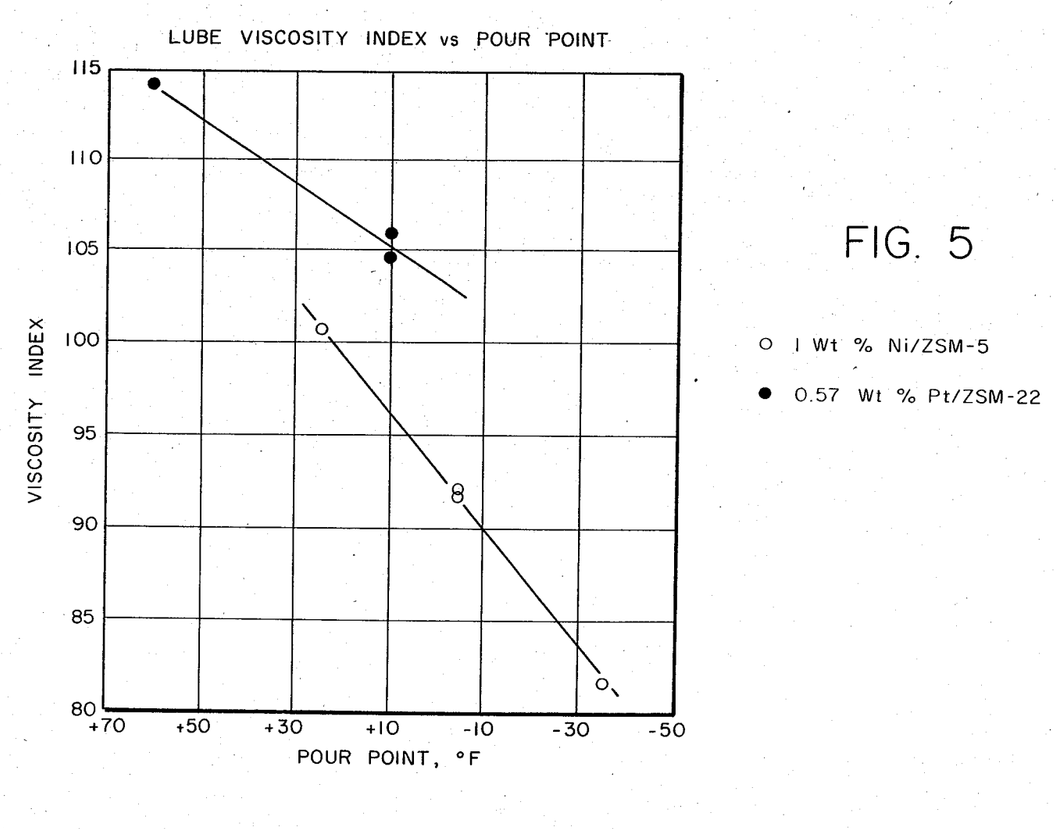
FIG. 5 is a plot of product viscosity index v. product pour point.

To compare the results of Examples 4 and 5, properties of the resulting hydrodewaxed stocks were compared in graphs of FIGS. 4 and 5 of the drawings. In FIGS. 4 and 5 lube yield and VI, respectively, are plotted against pour point. It can be seen that, at +10° F. pour point, both yield and VI with Pt/ZSM-22 are about 10 numbers higher compared to Ni/ZSM-5.

What is claimed is:

1. A process for hydrodewaxing a petroleum fraction having a boiling point above about 550° F., to produce a dewaxed lubricating oil base stock, comprising contacting a feedstock of said petroleum fraction, in the presence of hydrogen, with a supported catalyst composition comprising, in combination, about 20 to about 50 percent by weight of a support material; about 0.1 to about 3 weight percent of at least one Group VIII metal; the remainder being a porous crystalline silicate having a silicon to aluminum mole ratio, expressed in terms of the mole ratio of SiO₂ to Al₂O₃, of at least about 20, characterized by an X-ray diffraction pattern which is at least substantially identical to that of Table A, designated herein ZSM-22, wherein contact of said feedstock with said supported catalyst is undertaken under conditions including a pressure of from about 200 psig to about 3000 psig; a temperature of from about 260° C. to about 482° C.; a feedstock LHSV ranging from about 0.2 to about 20 and from about 500 and up to about 20,000 standard cubic feet of hydrogen per barrel of feedstock.

2. The process of claim 1, wherein said catalyst composition contains platinum.

3. The process of claim 1, wherein said catalyst consists essentially of said support material, platinum and said porous crystalline silicate.

4. The process of claim 1, wherein said support material is alumina.

5. The process of claim 3, wherein said support material is alumina.

6. The process of claim 1, wherein the activity and selectivity of the catalyst composition in which the Group VIII metal is selected from the group consisting of palladium, iridium, ruthenium, cobalt, nickel and admixtures thereof is substantially equivalent to that of the catalyst composition in which the Group VIII metal is platinum.

7. The process of claim 1, which includes the subsequent step of hydrotreating a product resulting from said contacting in the presence of hydrotreating catalyst under hydrotreating conditions including a temperature of from about 176° C. to about 371° C., a pressure of from about 1000 psig to about 3000 psig and a LHSV of from about 0.1 to about 10.

8. The process of claim 1, wherein said petroleum fraction is the effluent from a hydrocracking operation in which a hydrocarbon feedstock is hydrocracked in the presence of a hydrocracking catalyst at hydrocracking conditions including a temperature of from about 260° C. to about 482° C., a pressure of from about 1000 psig to about 3000 psig.

9. The process of claim 7, wherein said petroleum fraction is the effluent from a hydrocracking operation in which a hydrocarbon feedstock is hydrocracked in the presence of a hydrocracking catalyst at hydrocracking conditions including a temperature of from about 260° C. to about 482° C., a pressure of from about 1000 psig to about 3000 psig.

10. The process of claim 3, which includes the subsequent step of hydrotreating a product resulting from said contacting in the presence of hydrotreating catalyst under hydrotreating conditions including a temperature of from about 176° C. to about 371° C., a pressure of from about 1000 psig to about 3000 psig and a LHSV of from about 0.1 to about 10.

11. The process of claim 3, wherein said petroleum fraction is the effluent from a hydrocracking operation in which a hydrocarbon feedstock is hydrocracked in the presence of a hydrocracking catalyst at hydrocracking conditions including a temperature of from about 260° C. to about 482° C., a pressure of from about 1000 psig to about 3000 psig.

12. The process of claim 10, wherein said petroleum fraction is the effluent from a hydrocracking operation in which a hydrocarbon feedstock is hydrocracked in the presence of a hydrocracking catalyst at hydrocracking conditions including a temperature of from about 260° C. to about 482° C., a pressure of from about 1000 psig to about 3000 psig.

13. The process of claim 1, wherein the cubic feet of hydrogen per barrel of feed is at least about 2500.

* * * * *

UNITED STATES PATENT AND TRADEMARK OFFICE
CERTIFICATE OF CORRECTION

PATENT NO. : 4,574,043

DATED : March 4, 1986

INVENTOR(S) : Arthur W. Chester, William E. Garwood and James C. Vartuli

It is certified that error appears in the above-identified patent and that said Letters Patent is hereby corrected as shown below:

Column 2, line 4, change "$\pm$" to --"--.

Column 4, Table 1, insert *LHSV = liquid hourly space velocity, i.e. volumes of feed per volume of catalyst per hour.
**SCF = standard cubic feed per barrel--

Column 6, line 52, change "siiiceous" to --siliceous--.

Column 13, line 40, insert --Catalytic results with this catalyst are summarized below.--

Column 14, line 15, insert --Catalytic results with this catalyst are summarized below.--

Signed and Sealed this

Fourth Day of November, 1986

[SEAL]

*Attest:*

DONALD J. QUIGG

*Attesting Officer*    Commissioner of Patents and Trademarks